(12) United States Patent
Shaffer (10) Patent No.: US 9,392,874 B2
(45) Date of Patent: Jul. 19, 2016

(54) PRESSURE REDUCING DEVICE

(71) Applicant: David Shaffer, Flushing, NY (US)

(72) Inventor: David Shaffer, Flushing, NY (US)

( * ) Notice: Subject to any disclaimer, the term of this patent is extended or adjusted under 35 U.S.C. 154(b) by 0 days.

(21) Appl. No.: 14/685,813

(22) Filed: Apr. 14, 2015

(65) Prior Publication Data

US 2016/0113408 A1 Apr. 28, 2016

Related U.S. Application Data

(60) Provisional application No. 62/011,006, filed on Jun. 11, 2014.

(51) Int. Cl.
*A61G 7/075* (2006.01)
*A61G 13/12* (2006.01)
*A47C 20/00* (2006.01)
*A47G 9/10* (2006.01)

(52) U.S. Cl.
CPC ............... *A47C 20/021* (2013.01); *A47G 9/10* (2013.01); *A61G 7/0755* (2013.01); *A61G 13/1245* (2013.01); *A47G 2009/1018* (2013.01)

(58) Field of Classification Search
CPC . A61G 13/12; A61G 13/1205; A61G 13/123; A61G 13/1235; A61G 13/124; A61G 13/125; A61G 7/065; A61G 7/075; A61G 7/0755; A61G 13/1245; A61F 5/0102; A61F 5/0111; A61F 5/0118; A61F 5/01275; A61F 5/013; A61F 5/058; A61F 5/05858; A61F 5/0841; A61F 5/085; A61F 5/37; A61F 5/3723; A61F 5/3753; A61F 5/3761
USPC ............. 5/648, 650, 646, 647, 621, 623, 624; 602/5, 20, 21, 23, 24, 27; 128/845, 128/846, 877–879, 882
See application file for complete search history.

(56) References Cited

U.S. PATENT DOCUMENTS

| | | | |
|---|---|---|---|
| 2,712,311 A | 7/1955 | Scholl | |
| 3,462,775 A * | 8/1969 | Markwitz | A61F 5/01 128/889 |
| 3,903,878 A * | 9/1975 | Spann | A61F 13/069 128/892 |
| 3,931,654 A * | 1/1976 | Spann | A61G 7/0755 5/650 |
| 4,104,746 A * | 8/1978 | Goetz | A61F 13/069 5/650 |
| 4,186,738 A * | 2/1980 | Schleicher | A61F 13/069 128/892 |
| 4,323,610 A * | 4/1982 | Leverich | A47B 95/043 428/100 |
| 4,573,456 A * | 3/1986 | Spann | A61F 13/069 602/27 |
| 4,982,745 A * | 1/1991 | Shields | A61F 5/01 128/877 |
| 5,085,214 A * | 2/1992 | Barrett | A61F 5/01 128/882 |
| 5,418,991 A * | 5/1995 | Shiflett | A47C 20/021 5/647 |
| 5,449,339 A * | 9/1995 | Drennan | A61F 5/0195 128/882 |
| 5,618,263 A * | 4/1997 | Alivizatos | A61F 5/05841 128/878 |
| 5,839,139 A * | 11/1998 | Fink | A61G 7/0755 5/648 |
| 5,882,324 A | 3/1999 | Baranowski | |

(Continued)

OTHER PUBLICATIONS

4" Foot elevator found in market, picture attached herein.

*Primary Examiner* — Robert G Santos (57) ABSTRACT

A pressure reducing device for reducing pressure at bony prominences of limbs is disclosed. A preferred embodiment is formed of an elastic foam, having upper and lower portions similar to oppositely-facing square pyramids, but having four arced sides rather than flat sides, and where the four sides converge at their apexes to form a blunted peak. The cushion body is shaped and sized so as to reduce the loading and shearing forces over the bony prominences of limbs, thereby reducing pressure and to readily allow a user to move along the support surface and to change orientations (roll or lie on their side).

19 Claims, 10 Drawing Sheets

(56) References Cited

U.S. PATENT DOCUMENTS

| | | | | |
|---|---|---|---|---|
| 5,957,874 | A * | 9/1999 | Klein | A61F 5/0195 128/882 |
| 6,149,613 | A * | 11/2000 | Klein | A61F 5/0195 128/882 |
| 6,186,967 | B1 | 2/2001 | Messina | |
| 6,572,573 | B1 * | 6/2003 | Klein | A61F 5/0195 128/882 |
| 6,634,045 | B1 | 10/2003 | DuDonis | |
| 6,671,907 | B1 * | 1/2004 | Zuberi | A47G 9/1063 128/845 |
| 7,188,382 | B1 * | 3/2007 | Taylor | A61F 5/01 128/882 |
| 8,491,513 | B2 | 7/2013 | Flam | |
| 2005/0076445 | A1 * | 4/2005 | MacEachern | A47C 31/00 5/663 |
| 2007/0163048 | A1 * | 7/2007 | Kimball | A47C 20/021 5/632 |
| 2008/0028530 | A1 * | 2/2008 | Hao | A47G 9/10 5/647 |
| 2012/0061545 | A1 * | 3/2012 | Schneider | A47B 95/043 248/345.1 |
| 2013/0019410 | A1 * | 1/2013 | Willis | A47C 31/00 5/663 |
| 2016/0113408 | A1 * | 4/2016 | Shaffer | A47C 20/021 5/648 |

* cited by examiner

PRESSURE REDUCING DEVICE

RELATED APPLICATIONS

This patent application claims the benefit of U.S. provisional application 62/011,006, filed Jun. 11, 2014, the entire content of which is incorporated herein by reference into this application.

TECHNICAL FIELD

The invention relates to a stabilizing and protective device for limbs, especially for legs, by reducing pressure on bony prominences of the heels and ankles.

BACKGROUND

Ulceration of skin on a patient's feet is a common complication of diabetes and peripheral vascular disease. Ulcers can become so serious as to necessitate amputation. Ulcers can occur on any part of the foot, but the bony prominences of the heels and the ankles are especially vulnerable for a bedridden patient. The ulcers result in decreased pain sensation which can cause abnormal loading of the feet, increased localized pressure and formation of callouses, which cause tissue damage. The ulcers are primarily treated by ensuring an adequate blood supply; treating the underlying infection with appropriate antibioics; and by relieving the pressure on the affected part.

Pressure ulcers (also known as bed sores) often develop in individuals confined for an extended period to a particular position in a bed or chair. The pressure ulcers can be treated by managing tissue loads, including direct pressure, friction, and shear, through positioning techniques and use of appropriate support surfaces. For example, positioning devices can be used to raise a heel ulcer off the support surface and prevent direct contact between the surface and bony prominences. Past solutions include padding the heel area. But this is often ineffective because the pressure between the padding and the heel may remain significant enough to still cause ulceration, and, moreover, padding will reduce circulation of air about the heel which normally aids in healing of ulcers.

Another conventional means for reducing heel pressure is using a foot and leg protector having a rigid outer shell with an inner soft protective liner. However, the protector includes wrapping or adjusting straps which may cause added pressures on the skin, and reduce blood flow. Additionally, the user has to move, adjust or remove the straps frequently which is inconvenient, uncomfortable and may not be possible for a seriously disabled patient.

Protective devices without straps include a pressure resilient cushion that is adapted to be positioned under a bony prominence (including the knee joint or heel). The pad includes a relatively flat surface conformable to the skin area which it protects. The pad preferably includes a recess to surround the bony prominence, and a section around the recess that abuts, supports and cushions the region around the prominence. However such pads do not maintain the prominence of ankle, heel and elbow at a sufficiently elevated position and, again, significant pressure against the heel may remain when the pad is employed.

Surrounding the limb with a cylindrical padding, or placing a cushion under the calf does elevate the limb. But a cushion does not roll when the patient does so in bed. While cylindrical padding can roll with the patient, it cannot stabilize the limb when the bed surface suddenly deforms (such as by the plaintiff moving his other leg or limbs, or resting an object on or someone suddenly sitting on the bed).

Therefore, there is a need for a device to reduce pressure at the bony prominences of heels, ankles and elbows, which can move with the patient in bed and stabilize the limbs against the bed surface moving.

SUMMARY

A preferred embodiment is a device formed of an elastic foam, preferably latex foam or memory foam. The upper and lower portions are preferably similar to oppositely-facing square pyramids, but having four arced sides rather than flat sides, and where the four sides converge at their apexes (which is positioned furthest from the limb when the limb is inside the channel in place) to form a blunted peak. The device has a longitudinal separation separating the upper portion into two halves. The separation runs along the length of a channel designed to accommodate the patient's limb. The limb is inserted into the channel by first widening the separation and putting the limb in place, then narrowing the opposing halves of the upper portion and closing the two halves about the limb using a strap or fastener system.

To support a user's leg, the channel is of a length so as to surround the region from either above the knee (to protect it) or from just below the knee, to above the ankle. When the patient is lying supine, the bottom portion provides elevation of the ankle and heel from the bed surface. The flexible foam distributes the weight of the leg over the surface of the channel which contacts the underside of the leg. To avoid excessive heat build-up and increase comfort, the tension adjustment is preferably loose enough to provide a gap between the upper surfaces of the user's limb and the adjacent portions of the device.

The arced, square-pyramidal shape of the upper and lower portions (made of an elastic foam), at their respective apexes provides a movement dampening effect, and reduces the responsive movement of the limb even if the mattress upper surface moves vertically quickly. The region of the upper and lower portions near the apexes can compress readily (due to its reduced cross section) and provide such additional movement dampening. When the user lies prone, the upper portion provides the same movement dampening effect, as then the leg weight is resting on the apex in the upper portion. If the user lies on his/her side, the side portions of the foam device provide cushioning and also, facilitates rolling because of its arced shape. It also facilitates having the user roll on his/her side, to where the weight of the limb rests on one of the laterally facing surfaces of the square pyramid, and provides added comfort for the user when lying on his/her side. The shape of the upper and lower portions and the elastic foam material also facilitates movement of the patient longitudinally on the bed. The blunted peak and the two triangle sides provides a "rocking chair" type of assistance to ease out the back and forth movement of the leg. In addition, as the stored energy in the foam from the weight of the user's limb facilitates lifting the weight of the user's limb upwardly, and then the user can inch along the bed surface.

The strap or fastener which closes the channel around the limb is preferably adjustable, and can more preferably be a hook and loop fastener. This adjusting means is adaptable to provide breathability, and help prevent ulcers forming on the bony prominences of limbs, including heels, ankles, knees, and elbows. Finally, this system would allow quick and easy access to any ulcers formed in these areas. As noted, the adjustment should be snug enough such that the device moves with the patient but such that air gaps remain between the limb and the channel.

To accommodate limbs with smaller cross-sections and ensure they fit snugly in the channel, one or more foam inserts, which preferably extend along the channel, can be used. To accommodate abnormally large limbs, including bandaged limbs or swollen limbs, an adjuster can be inserted in the channel to pry it open wider. The upper and/or lower portions of the device are preferably provided with ventilation holes from the outside to the channel, to increase air flow, transfer heat out, and increase patient comfort.

In other embodiments, the device can have the arced square pyramid shape for one portion, preferably the upper portion, and have the bottom portion flattened to distribute the leg weight over a larger surface area. A cylindrical cross section for the device, or an arc cross section for one portion with the other portion flattened or a square pyramid, is also among the embodiments.

BRIEF DESCRIPTION OF THE DRAWINGS

Elements in the figures have not necessarily been drawn to scale in order to enhance their clarity and improve understanding of these various elements and embodiments of the invention. Furthermore, elements that are known to be common and well understood to those in the industry are not depicted in order to provide a clear view of the various embodiments of the invention. Thus the drawings are generalized in form in the interest of clarity and conciseness.

DETAILED DESCRIPTION

Figure 1:
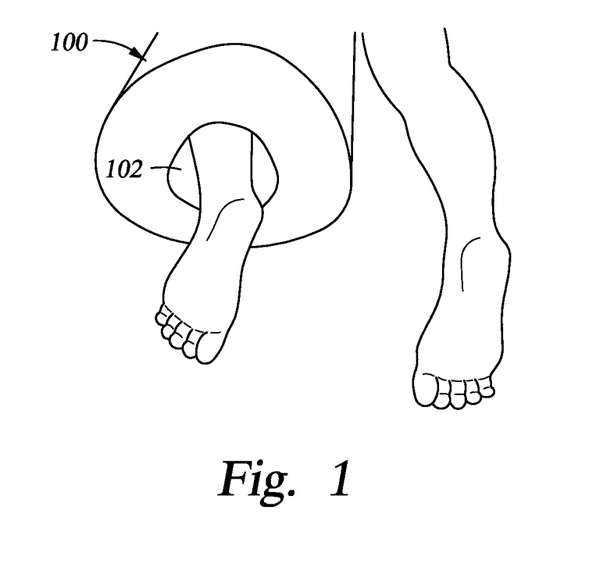
FIG. 1 is a perspective view of a preferred embodiment of the device, with a user's leg in place.
Figure 2:
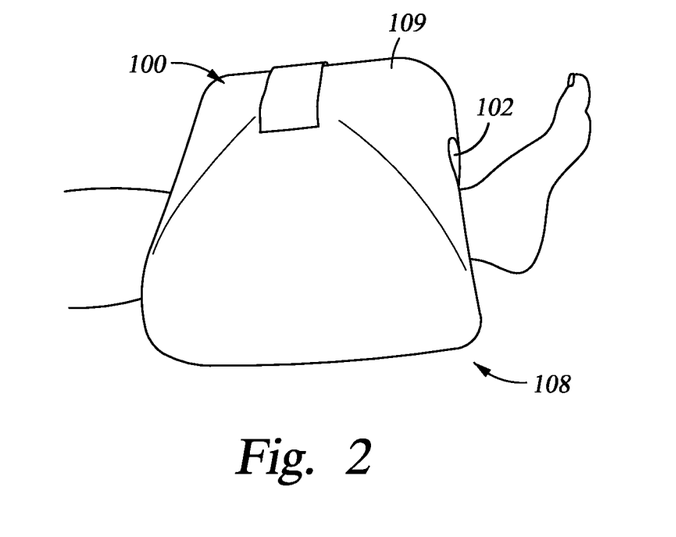
FIG. 2 is a perspective view of the preferred embodiment of the device from the side, with a user's leg in place.
Figure 3:
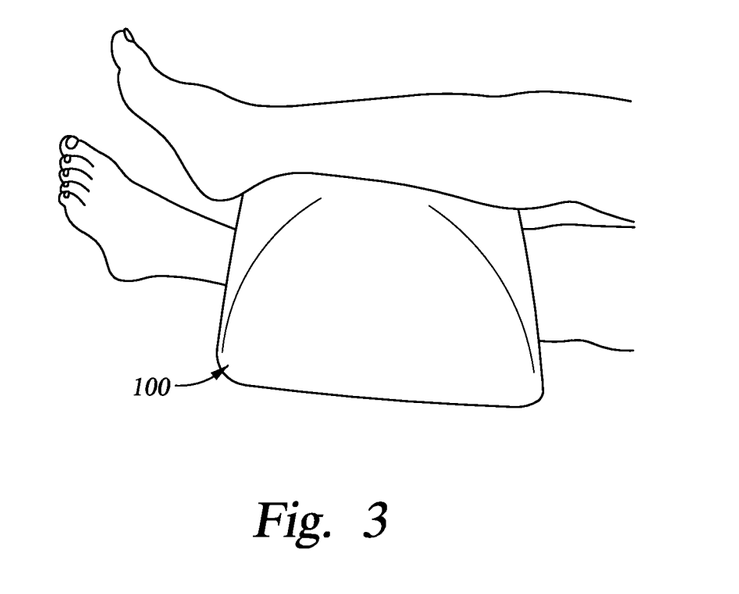
FIG. 3 is the same view as FIG. 2, but with the user's other leg positioned on top of the device.
Figure 4:
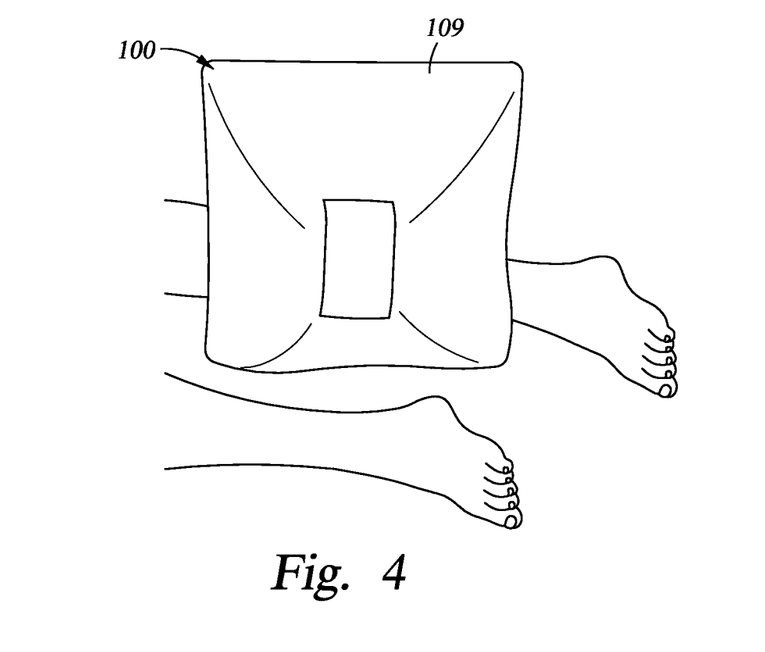
FIG. 4 is an elevational view, showing the user lying on their side.
Figure 5:
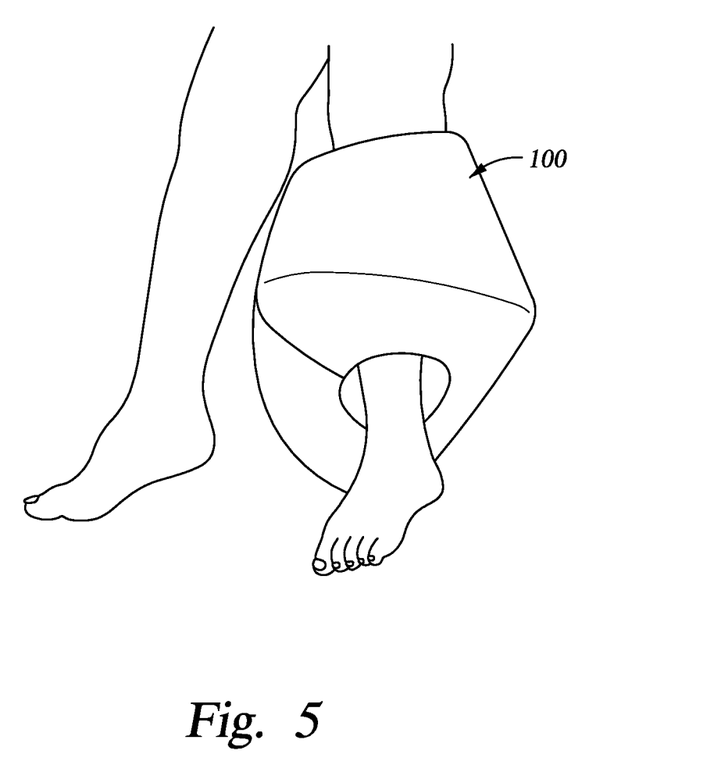
FIG. 5 is an elevational view from the end of the device, showing the user lying on their side.
Figure 6:
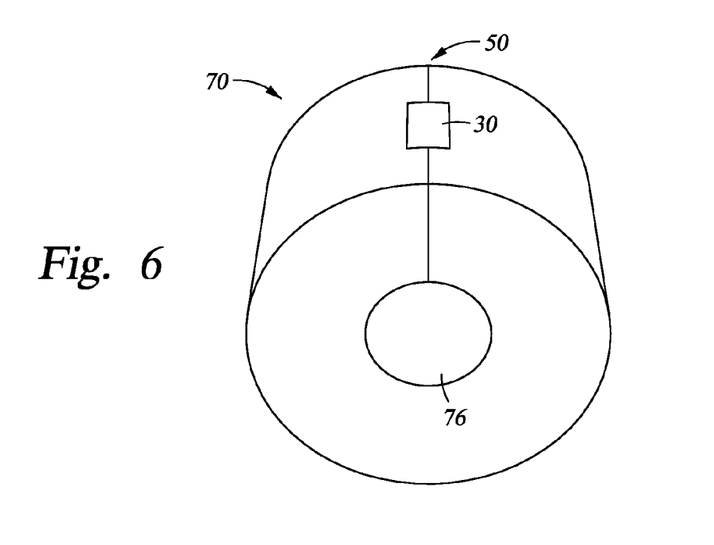
FIG. 6 is an elevational view of an embodiment of the device having a cylindrical cross-section.
Figure 7:
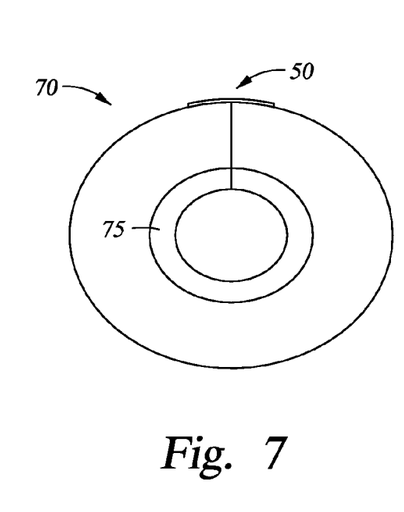
FIG. 7 is an elevational view from the end of the FIG. 6 embodiment, showing a foam insert for use in the channel of the device.
Figure 8:
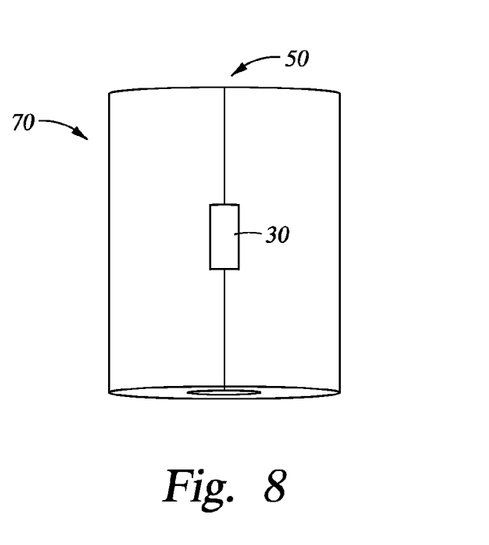
FIG. 8 is a plan view of the device shown in FIG. 6.
Figure 9:
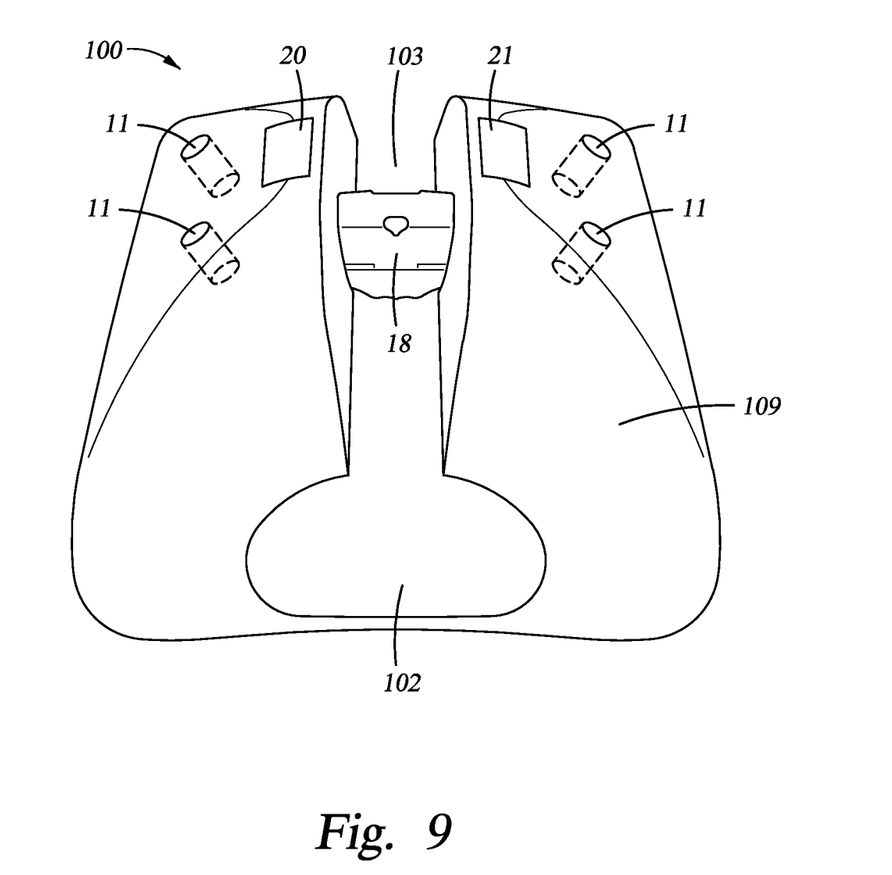
FIG. 9 is a perspective view of the preferred embodiment held in the open position.
Figure 10:
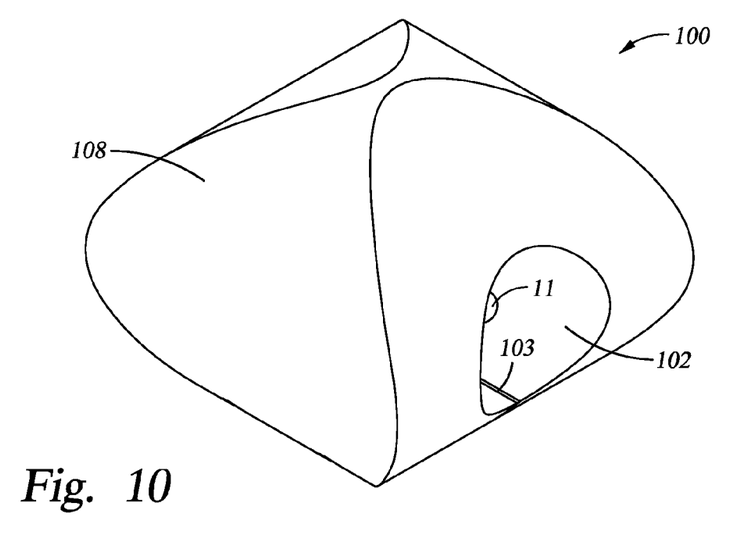
FIG. 10 is a perspective view showing the lower portion of the preferred embodiment.
Figure 11:
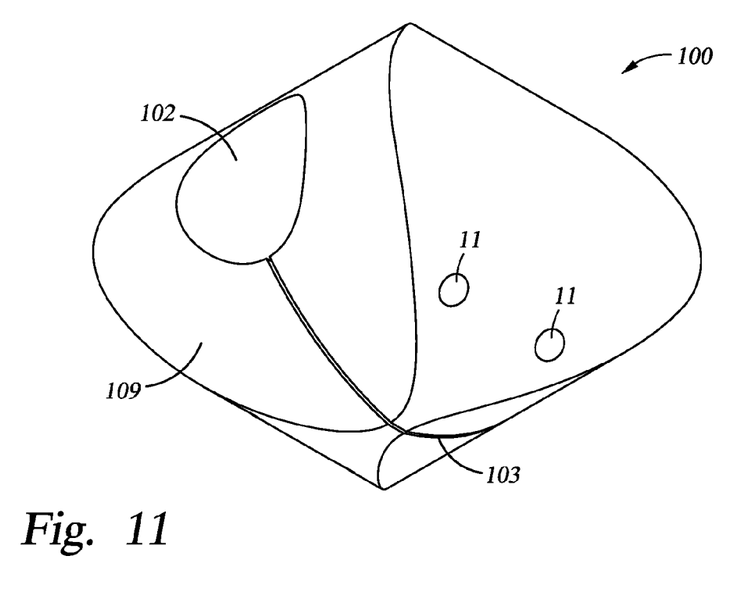
FIG. 11 is a perspective view showing the upper portion of the preferred embodiment.
Figure 12:
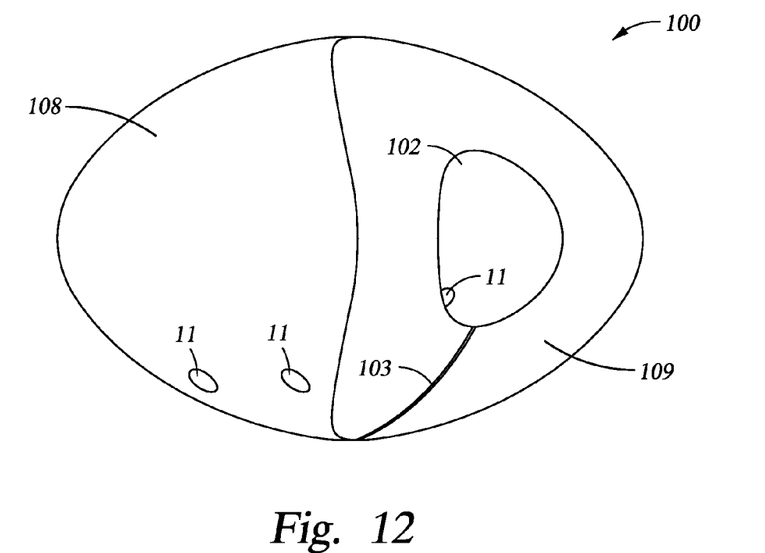
FIG. 12 is an elevational view from the front and side of the preferred embodiment.
Figure 13:
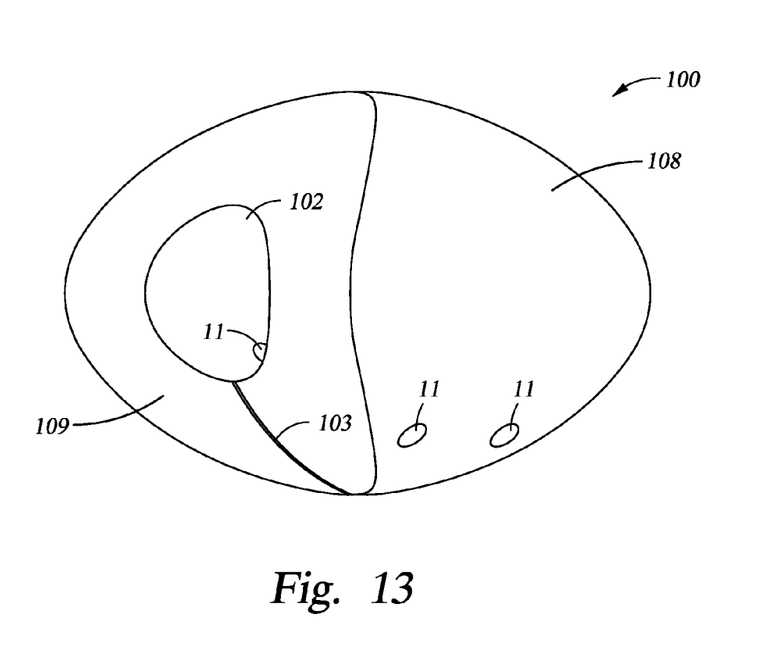
FIG. 13 is an elevational view from the front and the other side of the preferred embodiment.
Figure 14:
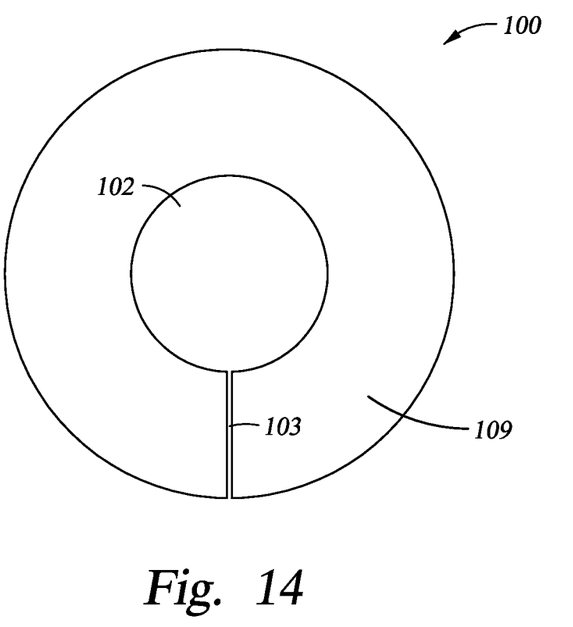
FIG. 14 is a cross-sectional view of the preferred embodiment.
Figure 15:
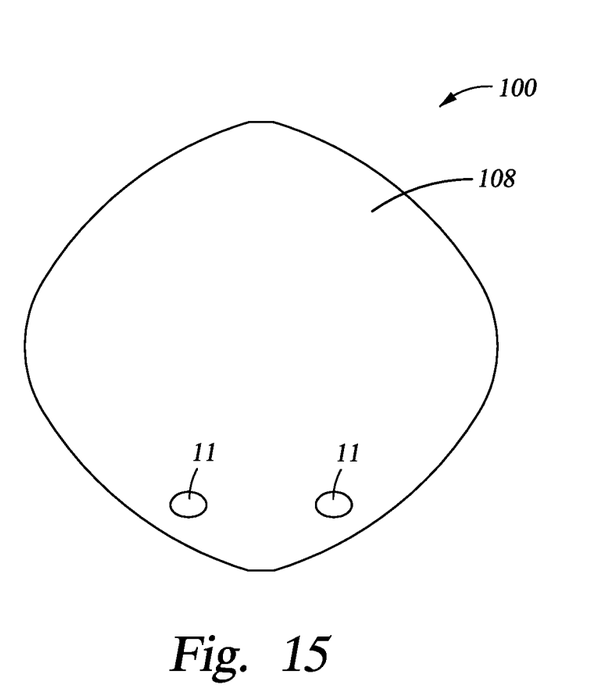
FIG. 15 is an elevational view from one side of the preferred embodiment.
Figure 16:
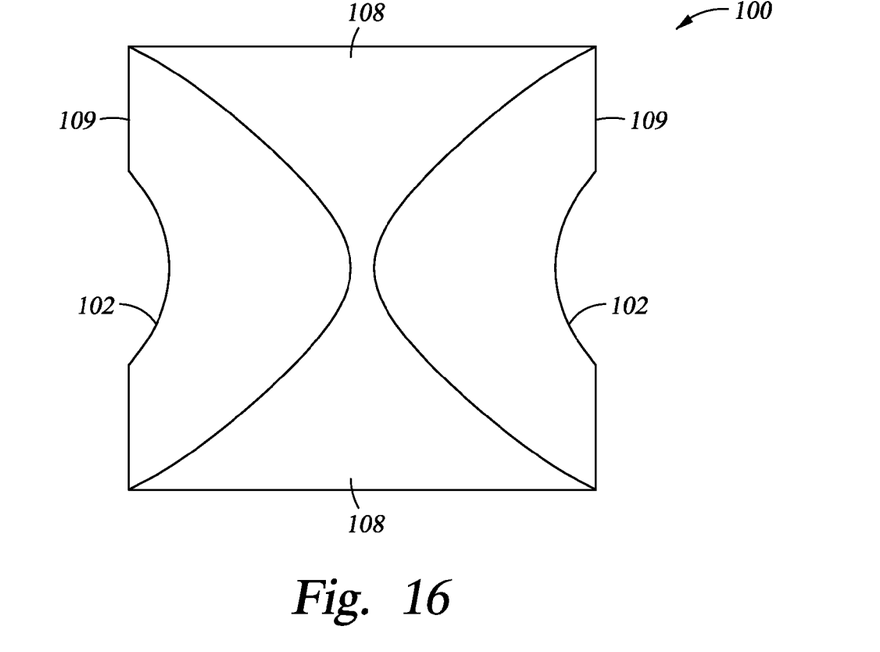
FIG. 16 is a plan view from the bottom of the preferred embodiment.
Figure 17:
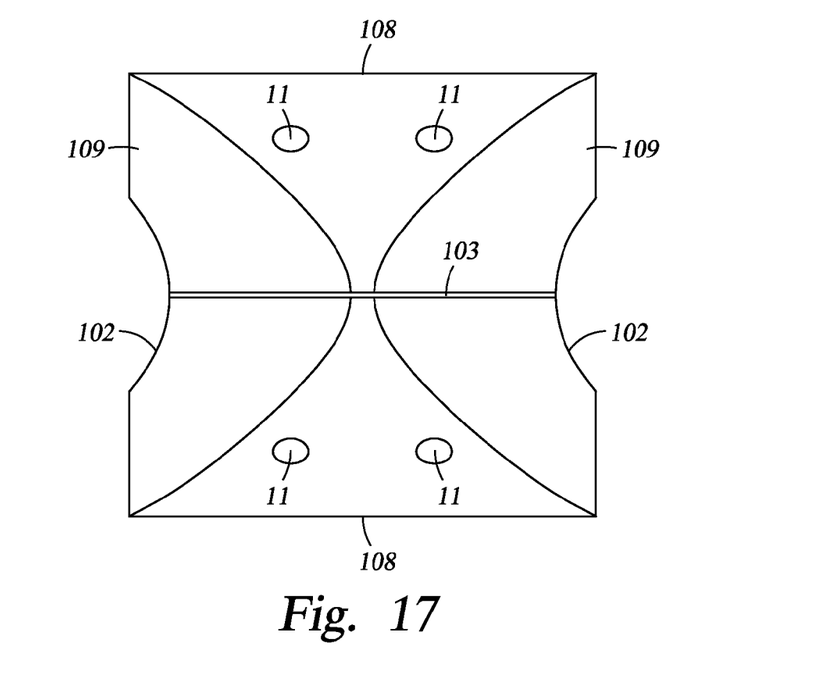
FIG. 17 is a plan view from the top of the preferred embodiment.
Figure 18:
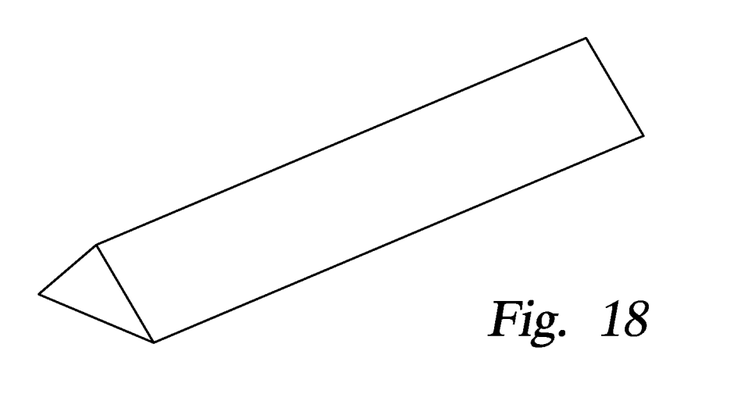
FIG. 18 is an elevational view of one type of insert for use in the channel of either embodiment of the device.
Figure 19:
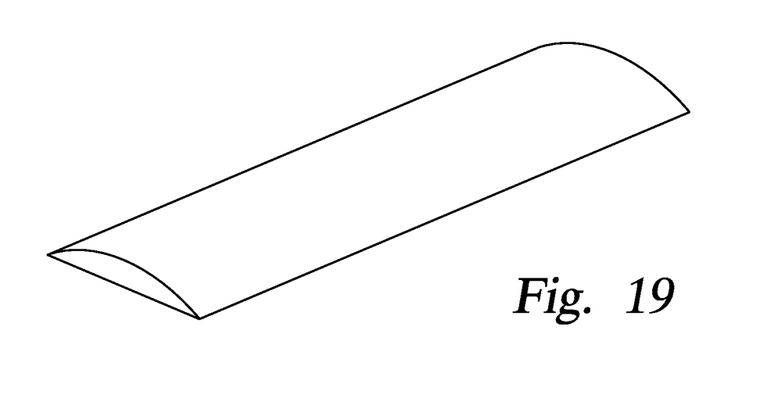
FIG. 19 is an elevational view of another type of insert for use in the channel of either embodiment of the device.
Figure 20:
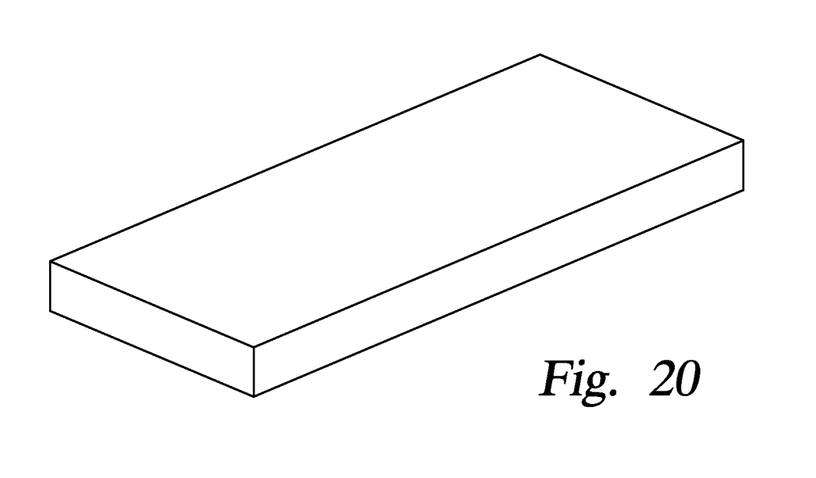
FIG. 20 is an elevational view of another type of insert for use in the channel of either embodiment of the device.

FIG. 1 depicts a user lying prone and using a first embodiment of a device 100 which, in this position, protects the user's bony prominences at his knees, ankle bones, heels, and toes. FIG. 2 depicts a user with device 100 in place and lying supine, with device 100 protecting the user's bony prominences at his knees, ankle bones, heels and toes. FIG. 3 depicts a user lying supine and resting his unprotected leg on top of device 100, with device 100 protecting the user's bony prominences at his knees, ankle bones, heels and toes in both legs. FIG. 4 depicts a user lying on his side with a device in place on his leg, with device 100 protecting the user's bony prominences at his knees, ankle bones, heels and toes. FIG. 5 is a plan view of a user lying on their right side, with device 100 protecting the user's bony prominences at his knees, ankle bones, heels and toes. FIG. 6 is an elevational view of another embodiment of the device 70 having a cylindrical cross-section. FIG. 7 is an elevational view from the end of the device 70, showing a foam insert 75 in place in channel 76 (shown in FIG. 6). FIG. 8 is a plan view of device 70. FIG. 9 is a perspective view of the preferred first embodiment 100 held in the open position about separation 103. FIG. 10 is a perspective view showing the lower portion 108 of device 100. FIG. 11 shows the upper portion 109 of the device 100. In FIGS. 12 and 13 device 100 is inverted and viewed from the side. FIG. 13 is an elevational view from the front and the other side of the preferred embodiment. FIG. 14 is a cross-sectional view of device 100 viewed along channel 102. FIG. 15 is another side elevational view of device 100. FIG. 16 is a plan view of the bottom 108 of device 100. FIG. 17 is a plan view from the upper section 109 of device 100. FIG. 18 is an elevational view of one type of insert for use in the channel of either embodiment of the device. FIG. 19 is an elevational view of another type of insert for use in the channel of either embodiment of the device. FIG. 20 is an elevational view of yet another type of insert for use in the channel of either embodiment of the device.

With the device 100 in use, the bony prominences of limbs (like, knees, ankle bones, heels, toes, elbows, for arms) are protected from contact with the mattress surface. FIGS. 1-5 show that the ankle bones, heels and toes of the limb in the device 100, are elevated away from the mattress surface, as are the knees. Alternatively, device 100 can be moved on the leg or lengthened so that the user's knee is also within channel 102, and thus protected. This position (around the knee), may be especially useful to reduce discomfort in patients having muscle contractions. With an arm in place in the device, and the hand extending out from the end, the bony parts of the hand and wrist as well as the elbow would be lifted out of contact with the surface a user was lying on, and thus protected.

By reducing pressure at bony prominences of limbs, device 100 protects against pressure sores, bed sores (for those confined to bed for long periods) and ulcers. The bony prominences are areas of the body that are at the greatest risk for developing pressure sores and ulcers, which are common complications of diabetes and peripheral vascular disease. Treatment of ulcers requires insuring that there is adequate blood supply, treating the underlying infection with the appropriate antibiotics and relieving the pressure of the affected part. Decreased pain sensation associated with diabetes can lead to abnormal loading of the foot causing increased localized pressure, which results in callouses leading to tissue damage. Device 100 reduces both direct loading forces and shearing forces (when the user moves) over the bony prominences of the limbs.

Device 100 permits the user to lie on their front, side, and back and still protect the bony limb prominences, by either padding them, or elevating them from the bed surface.

In use, the user can lie prone, supine or on their side (as shown in FIGS. 1-5.) When the user lies on their side, the arced surfaces of the upper portion 109 or the lower portion 108, can lie on a flat surface, like a mattress-top, and increase user comfort. FIG. 3 shows that when lying supine, the user's comfort can be enhanced by placing the other leg on top of the device 100.

FIGS. 6-8 show another embodiment of device, which is device 70, having a cylindrical cross-section. Device 70 accommodates a user's leg in its channel 76, and following insertion of the limb, the split 50 is closed with hook and loop fastener 30. Device 70 can be used with a cylindrical insert 75 (FIG. 7) to accommodate thin limbs, including arms, and provide a better fit.

In FIGS. 9-17, the preferred embodiment of device 100 has separation 103 between the two halves of the upper portion 109, and channel 102 designed to accommodate a patient's limb. The two portions of a hook and loop fastener, 20 and 21, are affixed to either side of the separation 103, are not in the closed position (attached to each other). Separator 18 maintains the separation of the two halves of the upper portion 109 against the elasticity of the foam device 100 (which tends to draw the two halves of upper portion 109 together). Ventilation holes 11 in the upper portion 109 run from the outside of device 100 and to the channel 102—to dissipate heat from the patient's limb and provide greater comfort.

The lower portion 108 (shown in FIG. 10) is designed to rest on a support surface e.g., a bed, sofa, mat, or any other generally horizontal surface capable of supporting the user's limb. The opening of separation 103 can be adjusted with the adjuster 18 (FIG. 9) to increase the size of the separation 103 so as to more readily admit and accommodate larger limbs. Since some users have bandaging and/or edema (swelling), the elasticity of device 100 allows accommodation of such limbs in channel 102. The device 100 is preferably adjusted after the limb is inserted to provide breathability to as much of the limb inside the device as possible, i.e., an air gap between the skin surface and the inside of the channel 102 is preferred.

Device 100 includes two oppositely-facing arced square pyramidal portions, upper portion 109 and lower portion 108, with a limb-accommodating channel 102 between the two portions and accessible by opening the upper portion 109 along separation 103. After the limb is in place, the separation 103 is closed by joining together the two parts 20 and 21 of the hook and loop fastener.

The devices of the invention may have their respective channels 102 or 76 fitted with a natural fabric liner (eg., cotton) liner, adding to the overall comfort and reducing the chance of an allergic reaction to the foam in these devices. The channels or other portions of these devices may also be treated with anti-fungal and/or anti-bacterial agents to preserve hygiene and reduce infection risk.

Among the advantages of the preferred embodiment 100 is that the patient's leg can readily move laterally or longitudinally along the bed, due to the reduced area (of either the upper 109 or lower portion 108, depending on whether the user is supine or prone) in contact with the bed, and because of the elasticity of the foam it's formed from (which absorbs energy to facilitate the patient's relieving the weight on the limb before moving it). This ease of movement aids comfort and health by encouraging shifting of the leg position, and thereby promoting circulation. With the user placing their other leg (with or without a device on that other leg) on top of the upper portion 109, as in FIG. 3, the design aids circulation and comfort for both legs.

Although Velcro™ fasteners having sections 20, 21 are preferred, a number of other means, such as straps or cords with buckles, clips or Velcro fasteners, or clips, buckles, elastic bands, ropes, strings, bungee cords, or other means can be used to draw the two halves of the upper portion 109 of the device around the user's limb. Any wrapping around the device should be used with caution, as it may cause added pressure on the limb and restrict blood flow.

In an exemplary embodiment, the length of channel 102 may be approximately 10.5-11.5 inches, while the diameter of channel 102 is approximately 5-6 inches.

FIGS. 18-20 each show a different type of insert which can be placed into channel 102 in order to accommodate smaller limbs more snugly, or, to elevate the user's foot or knee further from the surface the user rests on. The insert(s) selected would be inserted through the separation 103, either before or after the limb was in place. The device would then be closed about the limb. Optionally, the inserts can be fastened in place with cords or fasteners (including Velcro™).

In a first embodiment, there is a foam limb-support device for reducing pressure on heels and feet and other bony prominences for a user, comprising: an upper portion and a lower portion which are each shaped as oppositely-facing square pyramids having four converging arced sides; a channel extending through the device between the upper portion and the lower portion; and wherein, at least one of the upper portion and lower portion includes a separation running the length of the channel and dividing at least one said portion into two parts, such that when the two parts are separated, a user's limb can pass between the two parts and into the channel; and a means for fastening said two parts together, once the user's Limb is in place in the channel.

The means for fastening can be a hook and loop fastener, a strap, a cord, an elastic band, a bungee cord, a rope, a clip, a buckle or a re-useable adhesive. The device can be made of latex foam or memory foam. The device can include one or more ventilation holes extending from inside the channel to the outside of the device. The device can include an adjuster which can expand the channel. The adjuster can be made out of foam. The convergence of the triangular sides preferably forms a blunt ridge rather than a sharp peak. The four arced sides of the device are positioned such that a portion of one of the sides is on the upper surface of the bed when the user lies on his side. The device can include one or more inserts which can be positioned in the channel to more snugly accommodate a limb in the channel. The channel can be sized such that a substantial gap remains between the limb in the device and the adjacent inner surface of channel. The device can further include a natural fabric liner on the inner surface of the channel. The inner surface of the channel can be coated with anti-fungal and/or anti-bacterial agents.

In a second embodiment, there is a foam limb-support device for reducing pressure on heels and feet for a user, comprising: a substantially rectangular section made of an elastic foam designed to surround the user's limb; a means for fastening two edges of the rectangular section together. Once the user's limb is in place atop the rectangular section, a channel is formed surrounding the user's limb. The channel is sized such that a substantial gap remains between the limb and the adjacent inner surface of channel. The device can include a foam insert which is positioned immediately adjacent the user's limb when the limb is in place in the device. The device can be made of latex foam or memory foam. The device can further include one or more ventilation holes extending through the section. The means for fastening can be a hook and loop fastener, a strap, a cord, an elastic band, a bungee cord, a rope, a clip, a buckle or a re-useable adhesive. The device can further include a natural fabric liner (like cotton) on the surface of the section adjacent the user's limb. The surface of the section adjacent the limb is coated with anti-fungal and/or anti-bacterial agents.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations. Although described in connection with preferred embodiments thereof, it will be appreciated by those skilled in the art that additions, deletions, modifications, and substitutions not specifically described may be made without departure from the spirit and scope of the invention as defined in the appended claims.

What is claimed is:

1. A foam limb-support device for reducing pressure on heels and feet and other bony prominences for a user, comprising:
    an upper portion and a lower portion which are each shaped as oppositely-facing square pyramids having four converging arced sides;
    a channel extending through the device between the upper portion and the lower portion;
    and wherein, at least one of the upper portion and lower portion includes a separation running the length of the channel and dividing at least one said portion into two parts, such that when the two parts are separated, a user's limb can pass between the two parts and into the channel; and
    a means for fastening said two parts together, once the user's limb is in place in the channel.

2. The foam limb-support device of claim 1 wherein said means for fastening is a hook and loop fastener, a strap, a cord, an elastic band, a bungee cord, a rope, a clip, a buckle or a re-useable adhesive.

3. The foam limb-support device of claim 1 which is made of latex foam or memory foam.

4. The foam limb-support device of claim 1 further including one or more ventilation holes extending from inside the channel to the outside of the device.

5. The foam limb-support device of claim 1 further including an adjuster which can expand the channel.

6. The foam limb-support device of claim 5 wherein the adjuster is made out of foam.

7. The foam limb-support device of claim 1 wherein the convergence of the triangular sides forms a blunt ridge rather than a sharp peak.

8. The foam limb-support device of claim 1 wherein the four arced sides are positioned such that a portion of one of the sides is on the upper surface of a bed when the user lies on his side.

9. The foam limb-support device of claim 1 further including one or more inserts which can be positioned in the channel to more snugly accommodate a limb in the channel.

10. The foam limb-support device of claim 1 wherein the channel is sized such that a substantial gap is configured to remain between the limb in the device and the adjacent inner surface of the channel.

11. The foam limb-support device of claim 1 further including a natural fabric liner on the inner surface of the channel.

12. The foam limb-support device of claim 1 wherein the inner surface of the channel is coated with anti-fungal and/or anti-bacterial agents.

13. A foam limb-support device for reducing pressure on heels and feet for an user, comprising:
    a substantially rectangular section made of an elastic foam designed to encircle a user's limb;
    said rectangular section is configured to roll up to form a through channel to encircle a user's limb; wherein said channel is sized such that a substantial gap is configured to remain between the limb and the adjacent inner surface of the channel; a means for fastening two edges of the rectangular section together; and further including one or more ventilation holes extending through the rectangular section.

14. The foam limb-support device of claim 13 further including a foam insert which is configured to be positioned immediately adjacent to the user's limb when the limb is placed in the channel.

15. The foam limb-support device of claim 13 which is made of latex foam or memory foam.

16. The foam limb-support device of claim 13 wherein said means for fastening is a hook and loop fastener, a strap, a cord, an elastic band, a bungee cord, a rope, a clip, a buckle or a re-useable adhesive.

17. The foam limb-support device of claim 13 further including a natural fabric liner on the inner surface of the channel.

18. The foam limb-support device of claim 17 wherein the natural fabric is cotton.

19. The foam limb-support device of claim 13 wherein the surface of the channel configured to be adjacent the limb is coated with anti-fungal and/or anti-bacterial agents.

* * * * *